United States Patent
O'Lenick et al.

(10) Patent No.: US 7,462,729 B1
(45) Date of Patent: Dec. 9, 2008

(54) SILICONE SPIDER ESTERS IN PERSONAL CARE APPLICATIONS

(75) Inventors: Kevin A. O'Lenick, Dacula, GA (US); Anthony J. O'Lenick, Jr., Dacula, GA (US)

(73) Assignee: SurfaTech Corporation, Dacula, GA (US)

( * ) Notice: Subject to any disclaimer, the term of this patent is extended or adjusted under 35 U.S.C. 154(b) by 677 days.

(21) Appl. No.: 11/150,640

(22) Filed: Jun. 13, 2005

Related U.S. Application Data

(63) Continuation-in-part of application No. 11/124,018, filed on May 9, 2005.

(51) Int. Cl.
*C07F 7/02* (2006.01)
(52) U.S. Cl. ..................... 554/77; 424/70.121
(58) Field of Classification Search ........................ None
See application file for complete search history.

(56) References Cited

U.S. PATENT DOCUMENTS

| 5,136,063 | A | * | 8/1992 | O'Lenick, Jr. ............... 554/77 |
| 5,334,372 | A | * | 8/1994 | Kawamata et al. ....... 424/78.03 |
| 6,362,353 | B1 | | 3/2002 | Ellis et al. |
| 6,891,051 | B1 | * | 5/2005 | Wohlman et al. ............. 554/77 |

* cited by examiner

*Primary Examiner*—Mp Woodward
*Assistant Examiner*—Bethany Barham

(57) ABSTRACT

The present invention is drawn to a process for providing emolliency to the skin using a series so called "silicone spider esters". These esters are derived from poly-hydroxy functional compounds sequentially reacted with ethylene oxide or propylene oxide, followed by the reaction of the alkoxylate with fatty acid. The resulting products are called silicone spider esters because they resemble the spider, wherein appendages are alkoxylated esters. The restrictions this orientation imposes on rotation allows for the preparation of polar esters that have little or no water solubility, and provide both moisturization to the skin and emolliency by reducing transepidermal water loss.

14 Claims, No Drawings

SILICONE SPIDER ESTERS IN PERSONAL CARE APPLICATIONS

RELATED APPLICATION

This application is a continuation in part of co-pending U.S. application Ser. No. 11/124,018 filed May 9, 2005.

FIELD OF THE INVENTION

The present invention is drawn to a process for providing emolliency to the skin using a series so called "silicone spider esters". These esters are derived from poly-hydroxy functional silicone compounds sequentially reacted with ethylene oxide or propylene oxide, followed by the reaction of the alkoxylate with fatty acid. The resulting products are called silicone spider esters because they resemble the spider, wherein appendages are alkoxylated esters. The restrictions this orientation imposes on rotation allows for the preparation of polar esters that have little or no water solubility, and provide both moisturization to the skin and emolliency by reducing transepidermal water loss.

BACKGROUND OF THE INVENTION

The use of alkoxyated non-ionic as surface active agents is well known. The ethoxylation of fatty alcohols results in compounds that have both water soluble and oil soluble groups. The result is a so called "surfactant", a contraction for surface active agent. The addition of ethylene oxide to fatty alcohol results in increasing water solubility.

The term "HLB" was first employed by the lab staff of the Atlas Powder Co. in America. This means the balance between the oil soluble and water soluble moieties in a surface active molecule, and is expressed as the "Hydrophile-Liphophile Balance". A more oil-soluble emulsifier shows a lower HLB and a more water-soluble emulsifier shows the reverse. HLB is a very useful method in selecting an emulsifier, but it still has several limitations to application for every surfactant.

The HLB system developed by Griffin some 50 years ago. The system depends upon the observation that the solubility of the surfactant is related to the percentage by weight of polyoxyalkylene portion of the molecule and is relatively independent of the nature of the fatty group.

HLB Value=% EO/5

| Water Dispersibility | HLB | % EO. |
| --- | --- | --- |
| Not dispersible | 1-4 | up to 20% |
| Poorly dispersible | 4-6 | 20%-30% |
| Milky dispersion | 6-8 | 30%-40% |
| Stable milky dispersion | 8-10 | 40%-50% |
| Translucent to clear | 10-13 | 50%-65% |
| Clear Solution | 13+ | Over 65% |

| HLB | Application. |
| --- | --- |
| 4-6 | W/O Emulsifier |
| 7-9 | Wetting Agent |
| 8-18 | O/W Emulsifier |
| 13-15 | Detergents |
| 15-18 | Solubilizers |

The HLB system has some very distinct situations I which the applicability breaks down. It is designed for ethoxylated products, specifically linear alcohol ethoxylates. It is not useful when applied to Guerbet alcohol ethoxylates due to the branching. We have also surprisingly and unrepentantly found that certain esters that are linked together through a linking group are not surfactants, despite high levels of ethoxylates. We have dubbed these silicone spider esters since the structure is reminiscent of a spider. The crosslinking group is the body of the spider and the ethoxylated fatty esters are the legs. A specific order is also needed. The ethoxylated needs to be closest to the body of the spider and the fatty group at the foot end. While not wanting to be limited by any one theory we believe this orientation limits rotation of the polyoxyalkylene group and causes the molecule to be incapable of orientation at the surface of a water oil interface. Such orientation results in water solubility caused by the polyoxyalkylene groups going into the water and the oil soluble group going into the oil phase. The result is an ester that contains an appreciable amount of polar polyoxyalkylene group but is water insoluble. This is a very interesting material in that it represents a polar rich oil in which polar and ionic materials may be dissolved and applied in an oil phase. This is a critical concept for delivery of antioxidants, free radical scavengers, sun screens and the like to the skin.

Surfactants are by definition compounds that remove natural oils from the skin. The removal of oil from the skin is a stripping process that damages the skin and provides dry chapped skin. Surfactants in the process of emulsification, detergency or wetting have a cleansing effect in removing soil form the skin, but concurrently cause dry skin. This process results in dry skin and cosmetically unacceptable appearance to the skin. Dry skin is a major consumer problem in the cosmetic industry.

It is generally accepted that there are two different mechanisms of providing emolliency to the skin. The first is to provide moisture in so called moisturizing compounds. These compounds allow moisture to penetrate the skin. The alternate method is to trap moisture inside the skin providing a barrier that does not allow moisture to be lost. The barrier is a water insoluble oil that when placed on the skin keeps moisture from evaporating. It is clear that the two different mechanisms are mutually exclusive. That is, if an emollient oil is applied to the skin, not only can moisture not exit the skin, but moisture cannot enter, traversing the barrier. If a moisturizer is applied to the skin it must be applied to a barrier free skin. Simply put you cannot have effective moisturization on skin with a barrier present, since it will not penetrate. There is a long felt need for a technology that provides moisturization and emolliency. This requires a non-surface active polar oil that can simultaneously have water binding sites and oil soluble sites. Such a combination of properties has been elusive until the process of the current invention was discovered.

U.S. Pat. No. 5,136,063 issued to O'Lenick in August 1992 discloses a series of silicone esters that range in carbon length from $C_{12}$ to $C_{21}$. The compounds are claimed to provide outstanding softening and lubricating when applied to textiles and fibers. The patent states: "It is the object of the present invention to provide novel silicone based fatty ester compounds which are substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds, which are insoluble in those materials."

As will become clear from the teaching of the current invention, the patent U.S. Pat. No. 5,136,063 did not recognized that only by proper selection of the very short alkylene oxide groups could a product could be prepared that provides unexpected properties valuable properties which are the fact they are water insoluble oils.

We have unexpectantly and surprisingly found that molecules of the present invention, by virtue of having the polyoxyalkylene group bonded on one side to a fatty group and on the other to a common silicone backbone, compounds that have polyoxyalkylene contents that would render them water soluble if the they were present in non-silicone silicone spider esters. These polar esters link a fatty group through a polyoxyalkylene group to a common polymeric backbone. While not wanting to be held to one specific theory, the functionality of the present molecules has to do with the balance between the fatty group and the water soluble group and requires limitation on the orientation of the resulting polymer. The result is an ester that has little or no water solubility, an ability to deliver water and no surface activity.

By polyoxyalkylene groups is meant polyoxyethylene groups —(CH$_2$CH$_2$O)$_a$H), polyoxypropylene groups (—CH$_2$CH(CH$_3$)O)$_b$H) or mixtures thereof (—(CH$_2$CH$_2$O)a—CH$_2$CH(CH$_3$)O)$_b$H).

THE INVENTION

Object of the Invention

One objective of the present invention is to provide a series of unique silicone spider esters that are water insoluble yet contain polar groups. These polar groups solubilize ionic and polar materials providing delivery of polar materials that would otherwise be oil insoluble from a polar oil phase.

Another objective of the present invention is to provide a vehicle to improve oil solubility of antioxidants, sunscreens and free radical scavenger to allow for through and efficient delivery of these materials to the skin in a polar oil phase.

Other objects of the invention will become clear as one reads the following specifications and disclosures.

SUMMARY OF THE INVENTION

The present invention relates to a process for providing moisturization and emolliency to the skin in a simultaneous process. The process comprises contacting the skin with an effective moisturization concentration of a so called "silicone spider ester".

These so-called spider ester of the present invention have a fatty group connected through a short polyoxyalkylene group to a common linkage group. The so-called linkage group is a consequence of the choice of the proper poly-hydroxy compound. The resulting ester looks like a spider, having a silicone body (linkage group) and multi legs, having a low number of polyoxyalkylene groups present (the leg) and fatty ester groups (the spider's feet). This type of molecule allows groups that are oil soluble (fatty ester "feet"), water attracting (polyoxyalkylene groups (the spider's legs) and a linkage group (poly hydroxy raw material group). The compounds when applied to the skin allow for moisturization, by delivery of moisture from the spider's leg (polyoxyalkylene group), protection from evaporation of moisture (the spider's "fatty feet"), and no surface active properties, due to the lack of rotation caused by the linkage group, resulting in a very efficient multi-dimensional moisturizing agent. The process of using this compound in moisturization of the skin comprises contacting the skin with an effective moisturizing concentration of the silicone spider esters of the present invention.

DETAILED DESCRIPTION OF THE INVENTION

The spider ester of the present invention conforms to the following structure;

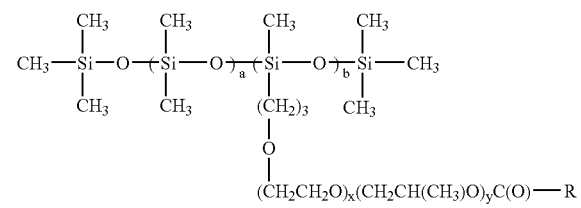

wherein;

a is an integer ranging from 0 to 20;

b is an integer ranging from 3 to 20;

x is an integer raging from 0 to 4;

y is an integer ranging from 0 to 4, with the proviso that x+y be less than or equal to 5;

R is alkyl having 7 to 32 carbon atoms.

PREFERRED EMBODIMENT

In a preferred embodiment a is 0; b is 3; x is 0; y is 0.
In a preferred embodiment a is 3; b is 5; x is 2; and y is 0.
In a preferred embodiment a is 5; b is 6; x is 0; and y is 2.
In a preferred embodiment a is 10; b is 5; x is 3; y is 2.
In a preferred embodiment a is 15; b is 10; x is 1; y is 0.
In a preferred embodiment a is 20; b is 5; x is 0; y is 1.
In a preferred embodiment a is 4; b is 10; x is 2; y is 3.
In a preferred embodiment wherein R is C7.
In a preferred embodiment wherein R is C11.
In a preferred embodiment wherein R is C17.
In a preferred embodiment wherein R is C21.
In a preferred embodiment wherein R is C36.

EXAMPLES FATTY ACIDS

Fatty acids useful as raw materials in the preparation of the compounds of the present invention are commercially available from a variety of sources including Procter and Gamble of Cincinnati Ohio. The structures are well known to those skilled in the art.

R—C(O)—OH

Saturated

| Example | R Formula | Common Name | Molecular Weight |
|---|---|---|---|
| | | Saturated | |
| 1 | $C_7H_5$ | caprylic | 144 |
| 2 | $C_9H_{19}$ | capric | 172 |
| 3 | $C_{11}H_{23}$ | lauric | 200 |
| 4 | $C_{13}H_{27}$ | myristic | 228 |
| 5 | $C_{14}H_{29}$ | pentadecanoic | 242 |
| 6 | $C_{15}H_{31}$ | palmitic | 256 |

-continued

| Example | R Formula | Common Name | Molecular Weight |
|---|---|---|---|
| 7 | $C_{17}H_{35}$ | stearic | 284 |
| 8 | $C_{19}H_{39}$ | arachidinic | 312 |
| 9 | $C_{21}H_{43}$ | behenic | 340 |
| 10 | $C_{26}H_{53}$ | cetrotic | 410 |
| 11 | $C_{33}H_{67}$ |  | 508 |
|  |  | Unsaturated |  |
| 12 | $C_{17}H_{33}$ | oleic | 282 |
| 13 | $C_{17}H_{31}$ | linoleic | 280 |
| 14 | $C_{17}H_{29}$ | linolenic | 278 |
| 15 | $C_{15}H_{29}$ | palmitoleic | 254 |
| 16 | $C_{13}H_{25}$ | myristicoleic | 226 |
| 17 | $C_{21}H_{41}$ | erucic | 338 |

Silicone Compounds

The silicone compounds useful in making the compounds of the present invention are commercially available from a variety of sources including Siltech LLC Dacula, G 30019. They conform to the following structure:

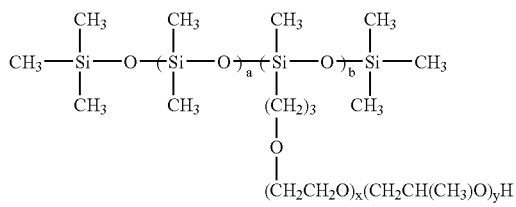

wherein;

a is an integer ranging from 0 to 20;

b is an integer ranging from 3 to 20;

x is an integer raging from 0 to 4;

y is an integer ranging from 0 to 4, with the proviso that x+y be less than or equal to 5;

| Example | a | b | x | y |
|---|---|---|---|---|
| 18 | 0 | 3 | 0 | 0 |
| 19 | 3 | 5 | 2 | 0 |
| 20 | 5 | 6 | 0 | 2 |
| 21 | 8 | 3 | 4 | 1 |
| 22 | 10 | 5 | 3 | 2 |
| 23 | 15 | 10 | 1 | 0 |
| 24 | 20 | 5 | 0 | 1 |
| 25 | 4 | 10 | 2 | 3 |

Preparation of the Compounds of the Present Invention

To a suitable reaction flask, equipped with agitator, a condenser, thermometer and ability to heat the contents to 200° C. is added, the specified number of grams of the specified fatty acid (Examples 1-17) is added the specified number of grams of the specified silicone compound (Examples 18-25). Next is added 0.1% by weight of stannous oxylate. The reaction mass is heated to between 180 and 200° C. When the temperature reaches about 160° C., water gins to distill off. The reaction is held for about 8-10 hours. After that time vacuum is slowly applied for about 3 additional hours, keeping the temperature within the specified range. The acid value becomes vanishingly low and the saponification value reaches theoretical.

| Example | Fatty Acid Example | Grams | Silicone Compound Example | Grams |
|---|---|---|---|---|
| 18 | 1 | 144.0 | 18 | 89.0 |
| 19 | 2 | 172.0 | 19 | 203.4 |
| 20 | 3 | 200.0 | 20 | 243.8 |
| 21 | 4 | 228.0 | 21 | 599.7 |
| 22 | 5 | 242.0 | 22 | 501.4 |
| 23 | 6 | 256.0 | 23 | 186.1 |
| 24 | 7 | 284.0 | 24 | 420.2 |
| 25 | 8 | 312.0 | 25 | 347.8 |
| 26 | 9 | 340.0 | 25 | 347.8 |
| 27 | 10 | 410.0 | 24 | 420.2 |
| 28 | 11 | 508.0 | 23 | 186.1 |
| 29 | 12 | 282.0 | 22 | 501.4 |
| 30 | 13 | 280.0 | 21 | 599.7 |
| 31 | 14 | 278.0 | 20 | 243.8 |
| 32 | 15 | 254.0 | 19 | 203.4 |
| 33 | 16 | 226.0 | 18 | 89.0 |
| 34 | 17 | 338.0 | 19 | 203.4 |

APPLICATIONS EXAMPLES

Despite the presence of the polyoxyalkylene groups and the polarity they introduce, the products of the present invention are insoluble in water. They do however have an unexpected ability to solubilize polar materials into the oil and not provide surfactant properties. The surface tension of all products is above 68 dynes/cm².

This ability to solubilize polar materials like fatty acids, alcohols, antioxidants, water soluble vitamins and the like provide an ability for formulate products in which polar actives can be delivered in an oil phase to skin or hair. The concept is particularly powerful in delivering actives like ascorbic acid which are water liable, turning dark very quickly in the presence of water.

If one goes through the standard HLB calculation it becomes clearly apparent that the molecules of the present invention fail to act like the predicted surfactants. We believe this is due in part to the short polyoxyalkylene oxide groups and the fact they are locked into the spider body at one side, limiting rotation needed to establish minimum free energy at the water interface, and the presence of the fully esterified fatty group on the far end of the spider's legs which destroy the polarity of the hydroxyl group. Silicone spider esters because of their unique structure are unique polar oils.

Typical of the properties of the silicone spider esters of the present invention are examples 25 and 30. Example 25 contains 40.2% by weight polyoxyalkylene group, having an HLB of 8.0. By HLB, this product should be milky in water forming a stable dispersion quite to the contrary it is a water insoluble oil. It is low in odor and has a very appealing feel on the skin. This silicone spider ester solubilizers sunscreens to a much greater extent than mineral oil. The product of example 30 can be emulsified as an oil using a HLB of 5.3 emulsifier to make a cosmetically acceptable water resistant sun screen. Example 30 provides outstanding moisturization to the skin when evaluated by consumer panel.

Example 25 is 40.2% polyoxyalkylene containing. It has an HLB of 8.0. By HLB, this product should be milky in water forming a stable dispersion quite to the contrary it is a water insoluble oil. It is low in odor and has a very appealing feel on the skin. This ester solubilizers sunscreens to a much greater extent than mineral oil. The product of example 25 can be used to solubilize a variety of antioxidants and deliver them in an oil to the skin, providing protection from UV degradation. Example 25 provides outstanding moisturization to the skin when evaluated by consumer panel.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claim be construed as encompassing all the features of patentable novelty which reside in the present invention, including all features which would be treated as equivalents thereof by those skilled in the art to which the invention pertains.

The invention claimed is:

1. A process for moisturizing the skin which comprises contacting the skin with an effective moisturizing concentration of a silicone spider ester conforming to the following structure;

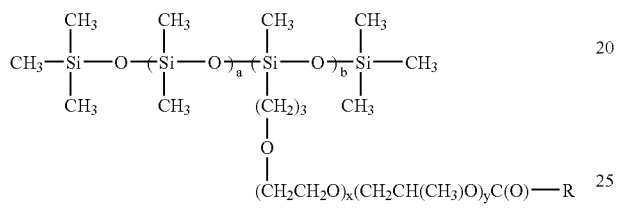

wherein;
   a is an integer ranging from 0 to 20;
   b is an integer ranging from 3 to 20;
   x is an integer raging from 0 to 4;
   y is an integer ranging from 0 to 4, with the proviso that x+y be less than or equal to 5;
   R is alkyl having 7 to 32 carbon atoms.

2. A process of claim 1 wherein a is 0; b is 3; x is 0; y is 0.

3. A process of claim 1 wherein a is 3; b is 5; x is 2; and y is 0.

4. A process of claim 1 wherein a is 5; b is 6; x is 0; and y is 2.

5. A process of claim 1 wherein a is 8; b is 3; x is 4; y is 1.

6. A process of claim 1 wherein a is 10; b is 5; x is 3; y is 2.

7. A process of claim 1 wherein a is 15; b is 10; x is 1; y is 0.

8. A process of claim 1 wherein a is 20; b is 5; x is 0; y is 1.

9. A process of claim 1 wherein a is 4; b is 10; x is 2; y is 3.

10. A process of claim 1 wherein R is C7.

11. A process of claim 1 wherein R is C11.

12. A process of claim 1 wherein R is C17.

13. A process of claim 1 wherein R is C21.

14. A process of claim 1 wherein R is C26.

* * * * *